United States Patent [19]

Tateosian et al.

[11] Patent Number: 5,477,054

[45] Date of Patent: * Dec. 19, 1995

[54] DENTURE CURING APPARATUS AND METHOD

[75] Inventors: Louis H. Tateosian, York; Duane E. Barber, Shrewsbury, both of Pa.

[73] Assignee: Dentsply Research & Development Corp., Milford, Del.

[ * ] Notice: The portion of the term of this patent subsequent to Mar. 21, 2012, has been disclaimed.

[21] Appl. No.: 217,571

[22] Filed: Mar. 25, 1994

Related U.S. Application Data

[63] Continuation of Ser. No. 987,101, Dec. 7, 1992, Pat. No. 5,298,758, which is a continuation of Ser. No. 693,212, Apr. 30, 1991, abandoned.

[51] Int. Cl.$^6$ .................................................. H01J 37/00
[52] U.S. Cl. .................... 250/492.1; 250/504 R
[58] Field of Search ............................. 250/492.1, 504 R

[56] References Cited

U.S. PATENT DOCUMENTS

| | | |
|---|---|---|
| D. 88,929 | 11/1932 | Moehler . |
| D. 308,976 | 7/1990 | Gonser . |
| 2,562,587 | 7/1948 | Swearingen . |
| 2,979,414 | 4/1961 | Ryshkewith . |
| 3,152,385 | 11/1961 | Wheildon et al. . |
| 3,309,772 | 3/1967 | Lieb et al. . |
| 3,325,629 | 6/1967 | Shelby . |
| 3,751,176 | 8/1973 | Von Hollen . |
| 4,203,690 | 5/1980 | Tanaka et al. . |
| 4,270,903 | 6/1981 | Nash . |
| 4,292,049 | 8/1981 | Tanaka et al. . |
| 4,304,576 | 12/1981 | Hatteri et al. . |
| 4,332,561 | 6/1982 | McSpadden . |
| 4,404,167 | 8/1983 | Bozenfeld et al. . |
| 4,412,134 | 10/1983 | Herold et al. . |

(List continued on next page.)

FOREIGN PATENT DOCUMENTS

| | | |
|---|---|---|
| 141303 | 6/1912 | Canada . |
| 279582 | 5/1927 | Canada . |
| 490545 | 2/1953 | Canada . |
| 971909 | 7/1975 | Canada . |
| 986455 | 3/1976 | Canada . |
| 1039680 | 10/1978 | Canada . |
| 1048965 | 2/1979 | Canada . |

(List continued on next page.)

OTHER PUBLICATIONS

TRIAD® VLC System; Technique Manual and Operating Service Manual; Dentply York Division; For Use With TRIAD® 2000 and TRIAD® II Curing Units; Sep. 1990.
TRIAD® II VLC Light Curing Unit; Dentsply York Division Operation and Service Manual; Feb. 1989.
Clinical Research Association Newsletter©; vol. 14, Issue 10; Oct., 1990 Subject: Resin Curing, Extroral Devices.
Tungsten Halogen Lamps; GTE Pennsylvania Engineering Bulletin 0–349.
Light Activated Composites, vol. 68, No. 11; Nov. 1989.
Skinner's Science of Dental Materials, 8th Edition; 1982.
1987 Operation and Service Manual.
Journal of Dental Research 70: Abstract No. 2368, 1991.
Dental Products Report, Nov. 1990; Cover page, back of cover page and p. 22.
Dental Products Report, Feb., 1991; Cover page, back of cover page and p. 49.

*Primary Examiner*—Bruce C. Anderson
*Attorney, Agent, or Firm*—Dale R. Lovercheck; Edward J. Hanson, Jr.

[57] ABSTRACT

An apparatus and method for curing light curable material using unfiltered light. A vented housing encloses a single lamp filament light source which emits visible light. The light source is positioned above and to the side of the light curable material which is supported on a rotating table during light curing. Light incident to the surface of the light curable material is at least about 50 milliwatts per square centimeter. The light curable material has a surface temperature of at least 150° F. (65.6° C.) after 2 minutes.

17 Claims, 3 Drawing Sheets

U.S. PATENT DOCUMENTS

| | | |
|---|---|---|
| 4,421,987 | 12/1983 | Herold . |
| 4,466,795 | 8/1984 | Plischka . |
| 4,538,070 | 8/1985 | Herold et al. . |
| 4,546,261 | 10/1985 | Gonser et al. . |
| 4,551,486 | 11/1985 | Tateosian et al. . |
| 4,552,491 | 11/1985 | Parker . |
| BI 4,571,665 | 4/1986 | Herold et al. . |
| 4,571,665 | 2/1986 | Herold et al. . |
| 4,582,998 | 4/1986 | Gonser et al. . |
| 4,611,400 | 9/1986 | Drake . |
| 4,625,119 | 11/1986 | Murdock, III . |
| 4,627,317 | 12/1986 | Komanduri et al. . |
| 4,681,541 | 7/1987 | Snaper . |
| 4,695,705 | 9/1987 | Kulig . |
| 4,698,206 | 10/1987 | Nevin . |
| 4,708,653 | 11/1987 | Eichen et al. . |
| 4,711,913 | 12/1987 | Tateosian et al. . |
| 4,734,624 | 3/1988 | Nagase et al. . |
| 4,760,509 | 7/1988 | Panagiotou . |
| 4,803,364 | 2/1989 | Ritter . |
| 4,839,521 | 6/1989 | Oppawsky . |
| 4,863,977 | 9/1989 | Tateosian et al. . |
| 4,873,446 | 10/1989 | Kreitmair et al. . |
| 5,298,758 | 3/1994 | Tateosian et al. . |

FOREIGN PATENT DOCUMENTS

| | | |
|---|---|---|
| 1059090 | 7/1979 | Canada . |
| 1059092 | 7/1979 | Canada . |
| 1064859 | 10/1979 | Canada . |
| 1067855 | 12/1979 | Canada . |
| 1100167 | 4/1981 | Canada . |
| 1122156 | 4/1982 | Canada . |
| 1176840 | 10/1984 | Canada . |
| 1193640 | 9/1985 | Canada . |
| 1194297 | 10/1985 | Canada . |
| 1202349 | 3/1986 | Canada . |
| 1203504 | 4/1986 | Canada . |
| 1229866 | 12/1987 | Canada . |
| 1238690 | 6/1988 | Canada . |
| 1255626 | 6/1989 | Canada . |
| 1258448 | 8/1989 | Canada . |
| 1262264 | 10/1989 | Canada . |
| 037461 | 10/1981 | European Pat. Off. . |
| 098602 | 11/1984 | European Pat. Off. . |
| 128324 | 12/1984 | European Pat. Off. . |
| 420369 | 4/1991 | European Pat. Off. . |
| 8619780 | 11/1986 | Germany . |
| 3825055 | 1/1990 | Germany . |
| 2098439 | 11/1982 | United Kingdom . |

DENTURE CURING APPARATUS AND METHOD

This is a continuation of U.S. patent application Ser. No. 07/987,101 filed Dec. 7, 1992 and U.S. Pat. No. 5,298,758, which is continuation of U.S. patent application Ser. No. 07/693,212 filed Apr. 30, 1991, now abandoned.

The invention relates to an apparatus and method for light curing of light curable material to form dental restorations and prosthetics in vitro. In particular the invention uses a single light source having a filament to cure light curable material. The apparatus of the invention has substantially reduced power consumption and equipment cost while at least maintaining the curing temperature provided by prior art light curing apparatus. The invention is particularly and especially preferred for use in the dental field in the construction and repair of dental appliances, such as retainers and dental prosthetics, for example dentures and bridges. The invention also has excellent characteristics allowing its expediant use in special medical applications, such as custom fabrication of hearing aids and finger splints.

Gonser et al in U.S. Pat. No. 4,546,261 disclose denture curing apparatus and method in which an array of light sources direct light in the 400 to 500 nanometer wavelength range onto a denture. Tateosian et al in U.S. Pat. Nos. 4,863,977; 4,711,913 and 4,551,486 disclose a process for preparing interpenetrating polymer network objects. These compositions are cured using light and/or heat. Such compositions have been cured in the four lamp denture curing apparatus of Gonser et all and a three lamp apparatus disclosed in Triad II VLC Light Curing Unit; Operation and Service Manual from Dentsply, 1987; which is also disclosed by Gonser U.S. Pat. No. Des. 308,976 (hereinafter referred to as Triad II).

Some prior art denture curing apparatus provide inadequate irradiant power to cure the light curable material. Prior art denture curing apparatus which do provide adequate irradiant power to cure light curable material use an array of tungsten filament light sources which are expensive. The prior art does not disclose an apparatus for denture curing which uses a single light source having a tungsten filament as is provided by the present invention. These problems of the prior art are overcome by the denture curing apparatus and method of the invention.

It is an object of the invention to provide an apparatus for denture curing using a single unfiltered light source having a tungsten filament and enclosing halogen gas.

It is an object of the invention to provide an apparatus for denture curing using a single unfiltered light source having a filament positioned within a vented housing.

It is an object of the invention to provide an apparatus for denture curing using a single unfiltered light source having a filament positioned above a rotatable table within a vented housing.

It is an object of the invention to provide an apparatus for denture curing which has reduced power consumption and reduced equipment cost while at least maintaining the curing temperature provided by prior art light curing apparatus.

It is an object of the invention to provide a method for curing dentures using light by providing a housing, a single filament light source, and polymerizable material in the form of a denture, and radiating light from the light source onto the polymerizable material to form a cured denture.

It is an object of the invention to provide a method for light curing light curable material at more than 70 milliwatts per square centimeter for at least 2 minutes while maintaining the material at least above 150° F. (65.6° C.).

The temperatures of the light curable material disclosed throughout this specification are surface temperatures which are generally uniform. Temperature measurements recited herein were made with a thermocouple probe having a digital readout.

Unfiltered light as used throughout this disclosure refers to light which is not subjected to means for removing specific wave lengths. While the glass enclosing the filament may remove insignificant amounts of light, the light passing therethrough is considered to be unfiltered.

Actinic light as used herein refers to light capable of initiating photochemical reactions. The light sources used in accordance with the invention provide actinic light.

The invention overcomes the problems of prior art light curing apparatus and methods through its useful, novel and nonobvious features. The advantages of the invention are not found in prior art light curing apparatus and methods.

BRIEF SUMMARY OF THE INVENTION

An apparatus and method for curing light curable material using unfiltered light. A vented housing encloses a single lamp filament light source which emits visible light. The light source is positioned above and to the side of the light curable material which is supported on a rotating table during light curing. Light incident to the surface of the light curable material is at least about 50 milliwatts per square centimeter. The light curable material has a surface temperature of at least 150° F. (65.6° C.) after 2 minutes.

DETAILED DESCRIPTION OF THE INVENTION

Figure 1:
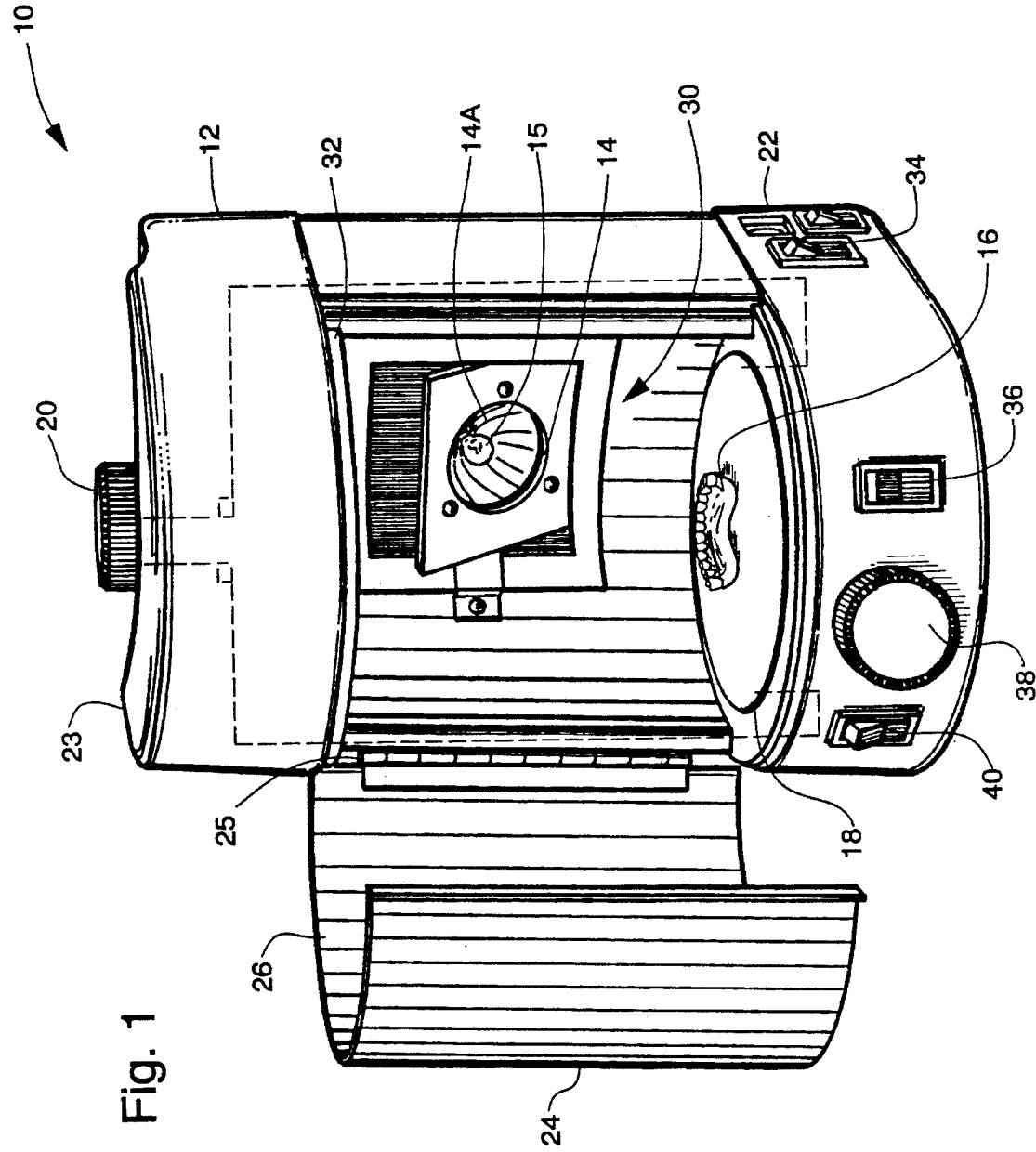
FIG. 1 is a perspective view of an apparatus for curing dentures in accordance with the invention.

The invention is now described in reference to the preferred embodiment shown in FIGS. 1–4 in which the same numerals refer to the same parts throughout the figures. FIG. 1 shows denture curing apparatus 10 which includes housing 12 and incandescent lamp 14. Preferably the lamp 14 includes a reflector 14A. Preferably the reflector has a surface which is adapted to distribute light, for example, by including smooth, faceted or peened surfaces. Incandescent lamp 14 has filament 15. Filament 15 is positioned within a trans-parent enclosure filled with a halogen gas or mixture of gases which is primarily halogen.

Light curable material 16 is supported on rotatable table 18. Urethane dimethacrylate resin with visible light activator may be used as the light curable material 16. The height of rotatable table 18 is adjustable by turning knob 20. Knob 20 is connected to a helical screw which turns through a helically threaded nut connected to a carriage which supports table 18.

Preferred light curable material for use in accordance with the invention is disclosed in U.S. Pat. No. 4,551,486 particularly at from column 1, line 46 to column 10, line 4, which is incorporated herein by reference. Preferred monomeric species useful in light curable denture making material are multifunctional and include acrylic and lower alkyl acrylic acid esters. In a preferred embodiment of the invention the light curable denture making material includes crosslinked polymer, filler, and crosslinking agent.

Figure 2:
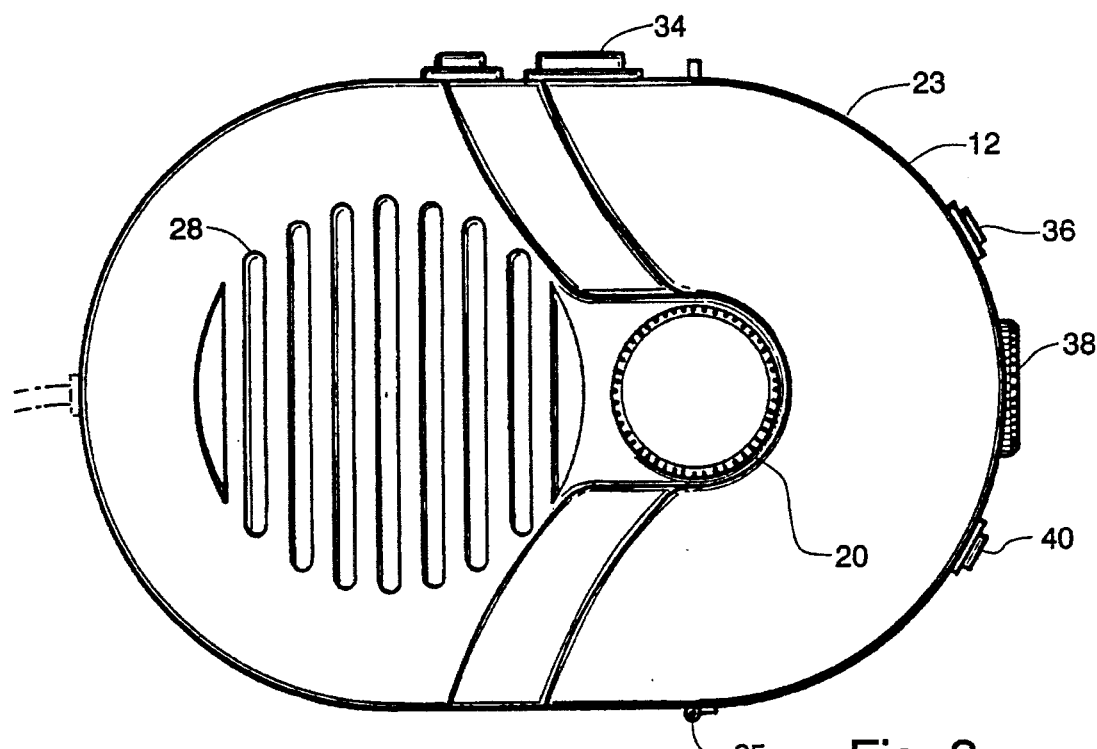
FIG. 2 is a top view of an apparatus for curing dentures in accordance with the invention.
Figure 3:
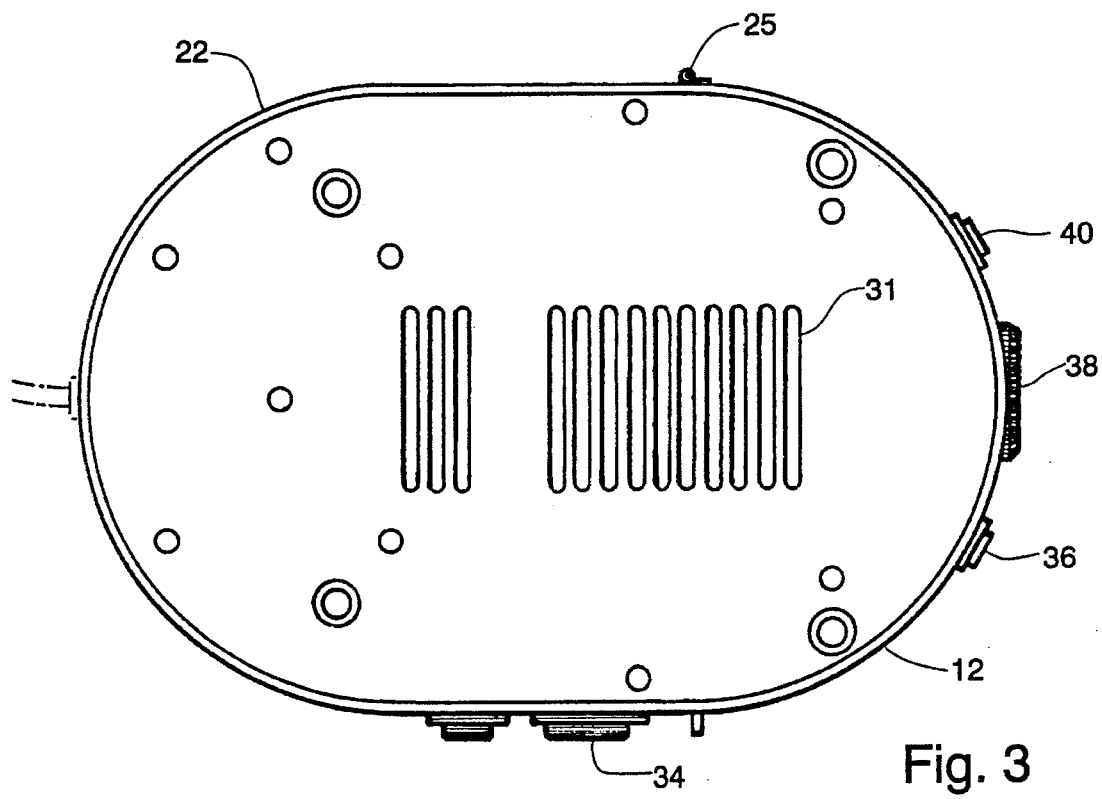
FIG. 3 is a bottom view of an apparatus for curing dentures in accordance with the invention.

Housing 12 has a base 22 and a top 23 as shown in FIGS. 1–3. Door 24 is connected by hinge 25 to base 22. Door 24 has reflective inner surface 26 which is adapted to reflect electromagnetic radiation from halogen containing incandescent lamp 14 onto light curable material 16. Upper vents 28 in top 23 allow heated air to be pulled by a fan from curing chamber 30 to the outside of the housing 12. Lower vents 31 allow air to pass through base 22 and enter curing chamber 30.

In use light curable material 16 is positioned within curing chamber 30. The width, depth and height of the curing chamber 30 are sufficient to allow dental restorations, prosthetics and appliances made of material 16 to be positioned therein.

Figure 4:
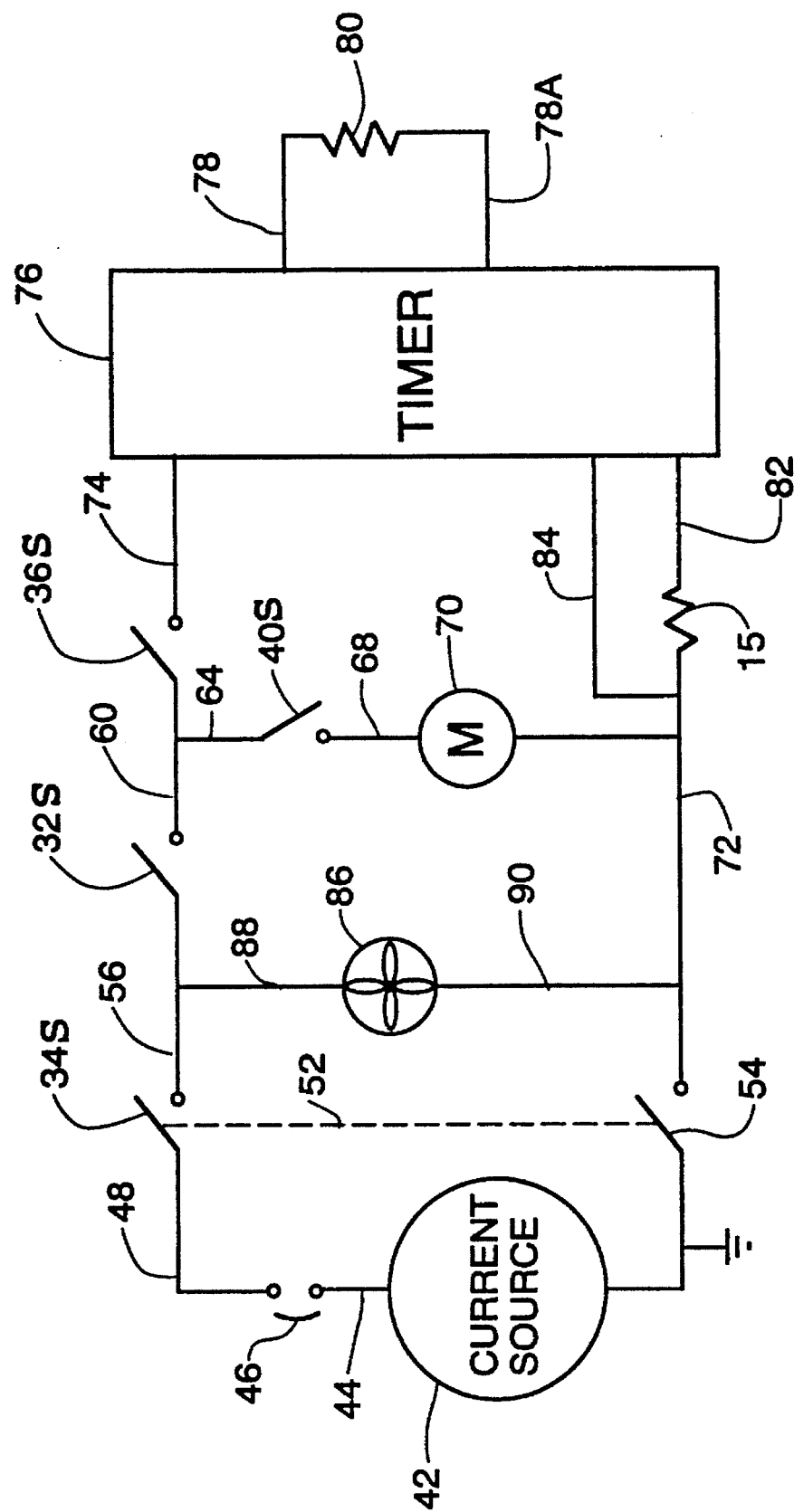
FIG. 4 is a schematic diagram of an electrical circuit of an apparatus for curing dentures in accordance with the invention.

With more particular reference to FIGS. 1 and 4 it is seen that door 24 in its closed position is adapted to press push button 32. When push button 32 is pressed switch 32S is in its closed position. Switches 34S and 36S are closed by pressing the power switch lever 34 and the cure switch lever 36. This permits electrical current to be conducted from current source 42 through tungsten filament 15 which emits infrared, visible and ultraviolet electromagnetic radiation. The period for cure is selected by setting the timer knob 38. Table switch lever 40 is adapted to actuate switch 40S.

Electrical current source 42 is connected through line 44 to circuit breaker 46. Circuit breaker 46 is connected through line 48 to switch 34S. Connector 52 operates switch 54 with switch 34S. Switch 34S is connected through line 56 to switch 32S. Switch 32S is connected through line 60 to switch 36S. Switch 32S is connected through line 64 to switch 40. Switch 40S is connected through line 68 to motor 70. Motor 70 is connected to ground through line 72. Switch 36S is connected through line 74 to timer circuit 76. Timer circuit 76 is connected through lines 78 and 78A to variable resistor 80. Timer circuit 76 is connected through line 82 to filament 15. Timer circuit 76 is connected to ground through line 84. Filament 15 is connected to ground through line 72. Fan 86 is connected to switch 34S through line 88. Fan 86 is connected to ground through line 90.

To cure light curable material 16 the dental technician places the material on table 18 and closes door 24 depressing push button 32, which closes switch 32S. The dental technician then depresses lever 34 which closes switches 34S and 54 which connects fan 86 to electrical current source 42. Then the dental technician depresses lever 40 which closes switch 40S connecting motor 70 to current source 42. The motor 70 turns table 18 which rotates material 16. Finally the operator rotates knob 38 to set timer 76, and presses lever 36 closing switch 36S to convey electrical current to filament 15. The material 16 cures in from about 2 to about 10 minutes at from about 120° to about 200° F. (93.3° C.) while being rotated in front of the light emitted from lamp 14. When the cure time has lapsed the dental technician removes the material 16 from table 18.

Preferably the filament is adapted to emit sufficient electromagnetic radiation to provide irradiant power on the upper surface of the curing material of at least 50 milliwatts per square centimeter. More preferably, the filament is adapted to emit sufficient electromagnetic radiation to provide irradiant power incident on the upper surface of the curing material of from about 50 to about 100 milliwatts per square centimeter.

Preferably the filament includes tungsten and is adapted to provide sufficient electromagnetic radiation to maintain the temperature of light curable material positioned within said housing at between 120° and 250° F. (48.9° and 121.1° C.).

Preferably the gas used to enclose the filament is argon or a mixture of argon and less than 1 percent by volume of other gases, such as bromine and nitrogen.

Preferably, the polymerizable material has a surface temperature of at least 150° F. (65.6° C.) after at least 2 minutes with less than 70 milliwatts per square inch of incident light. More preferably, the polymerizable material has a surface temperature of at least 145° F. (62.7° C.) after 10 minutes at less than 80 milliwatts per square inch of incident light.

Preferably the light source is positioned at an angle of from about 10 to about 60 degrees and a distance of from about 5 to about 13 cm above a support which is adapted to rotate light curable denture making material.

Preferably the product formed in accordance with the invention have a medical application. Most preferably the product formed in accordance with the invention is a denture, bridge, inlay or other dental prosthesis or hearing aid.

Preferably the motor is adapted to rotate the substantially horizontal upper surface of the table around a vertical axis of rotation. The lamp is positioned about 5 to about 13 cm from the center of the upper surface of the table. The filament is positioned above the center of the table an angle of from 10 to 45 degrees to the vertical axis of rotation.

A comparison is provided in the table below of typical temperatures and irradiant powers obtained using a prior art three lamp (200 watt tungsten halogen bulbs) light curing denture making apparatus (a Triad II) and a one lamp (250 watt tungsten halogen bulb) light curing denture making apparatus of the invention (a Triad 2000). The height of the top surface of the table in each apparatus is positioned where its center receives maximum irradiance. In this position the distance from the top of an about 0.2 inch thick disk of light curable material placed on the center of the table to the closest point on the filament is about 4 and ⅛ inch for the Triad II and about 4 and ¼ inch for the Triad 2000. The table is operated at 6 revolutions per minute. Each apparatus is connected to a 115 volt source. The temperature of the disk in each apparatus is measured after 10 minutes of illumination. The irradiant power during illumination is measured on the upper surface of each disk using a radiometer with a light guide and a 400 to 500 nanometer band pass filter.

TABLE

| Disk Temperature | Triad II (Prior Art) | Triad 2000 |
|---|---|---|
| (°F.) | 149 | 155 |
| (°C.) | 65 | 68.3 |
| Irradiant power (milliwatts per square centimeter) | 93.5 | 62.4 |

As shown in the Table above the invention typically provides higher temperatures for curing with about fifty percent less irradiant power. The advantages of the invention include reduced power consumption and reduced equipment cost while at least maintaining the curing temperature provided by prior art light curing apparatus. Additionally, apparatus in accordance with the invention (Triad 2000) provide superior curing of urethane dimethacrylate resin with visible light activator, note Clinical Research Associates Newsletter Volume 14, Issue 10 October 1990 paragraph 2A, the disclosure of which is incorporated herein by reference. The modulus of rupture and compressive strength of products produced in an apparatus in accordance with the invention (Triad 2000) is superior as shown in Bangerter et al, J. Dental Research 70: Abstract Paragraph No. 2368, 1991, the disclosure of which is incorporated herein by reference.

OPERATION

A moldable denture base putty-paste that is hardenable with visible light is formed according to U.S. Pat. No. 4,551,486 column 10, lines 15–68 and column 11, lines 1–2. The putty is pressed into a sheet and then adapted as a baseplate to a stone model (coated with separator) made from an impression of the mouth. The baseplate is trimmed and then cured for 2 minutes on the rotating table within the housing of an apparatus in accordance with the preferred embodiment of the invention shown in FIGS. 1–4: the TRIAD 2000 (available from Dentsply International: the assignee of the present patent application) under an unfiltered 250 watt tungsten halogen lamp: Dentsply International part number 70143. The electromagnetic radiation incident to the surface of the baseplate is about 80 milliwatts per square centimeter.

A 0.25 inch diameter rope of putty is adapted around the ridge of the baseplate in configuration to receive a pressed-in full arch of upper teeth formed as described at column 11, lines 50–55 of U.S. Pat. No. 4,551,486. A brush is used to apply bonding agent formed as described in column 11, lines 19–47 of U.S. Pat. No. 4,551,486 to an arch of teeth to cover the ridge lap areas and about 2 mm onto the facial, lingual collar and interproximal areas. After setting two minutes the bonding agent is then light cured in the TRIAD 2000 for two minutes as described above.

The arch of teeth is then pressed into the rope of putty on the baseplate, and then light cured in the TRIAD 2000 for two minutes as described above. An additional portion of putty rope is used to finish the facial and lingual aspects of the denture.

Liquid oxygen barrier is formed as described in U.S. Pat. No. 4,551,486 column 12, lines 12–28 and coated onto the top of the denture. The denture is cured for four minutes in the TRIAD 2000 as described above. The denture is then removed from the stone model and the other side of the denture is coated with liquid oxygen barrier and cured for two minutes in the TRIAD 2000 as described above. The denture is then washed in tape water and dried with a paper towel.

Further disclosure of the operation of apparatus in accordance with the invention is provided in Triad VLC system Technique Manual and Operation/Service Manual for Use With the Triad 2000 and Triad Curing Units, 1990, distributed by Dentsply International Inc. 570 West College Avenue, P.O. Box 872 York, Pa. 17405-0872, and incorporated herein by reference in its entirety.

Modulus of rupture, deflection at break, and elastic modulus as used throughout this disclosure is measured using ASTM D790 Transverse loaded beam. Izod impact as used throughout this disclosure is measured using ASTM D256.

Preferably highly filled products (having at least 25% inorganic filler) formed in accordance with the invention have a modulus of rupture of at least 6,000 psi, a deflection at break of at least 0.1 inch, an Izod impact of at least 0.7 ft-lb/in, and a depth of cure of at least 2 millimeters. Preferably, the products formed in accordance with the invention (having less than 25% inorganic filler) have a modulus of rupture of at least 11,000 psi, a deflection at break of at least 0.12 inch, an Izod impact of at least 1.3 ft-lb/in, and a depth of cure of at least 2 millimeters.

Preferably the width, depth and height of the light curing chamber in which light curable material is enclosed in accordance with the invention are each at least 2 inch. More preferably, the width, depth and height of the light curing chamber in which light curable material is enclosed in accordance with the invention are each at least 3 inch.

When the product and light source are in relative motion, preferably the light source is positioned above the product at an angle of from 10 to 45 degrees to the relative rotation of the product or the light source.

While in accordance with the patent statutes what is at present considered to be the preferred embodiment of the invention has been described it will be obvious to those skilled in the art that numerous changes and modifications may be made therein without departing from the invention, and it is therefore intended in the appended claims to cover all such equivalent variations as fall within the spirit and scope of the invention.

What is claimed is:

1. An apparatus for polymerization of light curable material, comprising:

a housing, and an incandescent lamp, having a filament and a gas, said lamp being supported and enclosed by said housing, said filament being enclosed by said gas, said gas comprising halogen gas, said filament providing sufficient electromagnetic radiation to maintain the temperature of said light curable material within said housing at between about 120° F. and about 250° F. and to substantially evenly cure said light curable material while rotating said light curable material.

2. The apparatus of claim 1 wherein said curable material is cured to form a denture.

3. The apparatus of claim 1 wherein said light bulb is the only source emitting electromagnetic radiation within said housing.

4. The apparatus of claim 1 wherein said housing further comprises a housing wall having at least one vent allowing air to pass out of said housing.

5. The apparatus of claim 1 further comprising a fan, said fan being supported by said housing.

6. The apparatus of claim 1 wherein said light source is operable using at least 200 watts of power to emit electromagnetic radiation, and provide at least about 50 milliwatts per square centimeter at a distance of about 10 cm.

7. The apparatus of claim 1 further comprising rotating means and a support member, said rotating means being connected to said support member, said support member being rotatable at a constant rate of rotation of from about 5 to about 25 revolutions per minute.

8. The apparatus of claim 1 further comprising rotating means and a support member, said rotation means being connected to rotate a substantially horizontal upper surface of said support member around a vertical axis which intersects a central point on said surface, said filament being positioned along a line extending through said central point at an angle of from 10 to 45 degrees to said axis, said filament being positioned from about 5 cm to about 13 cm from said central point, said filament being positioned above said support member.

9. The apparatus of claim 1 wherein said housing further comprises a door having a reflective inner surface.

10. The apparatus of claim 1 wherein said housing further comprises a door, said door comprising an optical filter which selectively reflects or absorbs electromagnetic radiation having wavelengths less than 400 nanometers.

11. The apparatus of claim 1 wherein said housing further comprises a chamber wall, said chamber wall having a reflective surface.

12. The apparatus of claim 1 wherein said electromagnetic radiation is unfiltered.

13. A system for polymerization of light curable material, comprising:

light curable material, a housing, and an incandescent lamp having a filament and a gas, said lamp being supported and enclosed by said housing, said filament being enclosed by said gas, said gas comprising halogen gas, said light curable material being enclosed by said housing, said filament providing sufficient electromagnetic radiation to maintain the temperature of said light curable material between about 120° F. and about 250° F. and said light curable material being substantially evenly cured by said radiation from said filament while rotating said light curable material within said housing.

14. The system of claim 13 wherein said curable material is cured to form a denture.

15. The system of claim 13 wherein said electromagnetic radiation from said light bulb effectively cures said light curable material.

16. A method of making a denture, comprising:

providing an apparatus for polymerization of light curable material, said apparatus having a housing, and an incandescent lamp having a filament and a gas, said lamp being supported and enclosed by said housing, said gas comprising a halogen, said filament providing sufficient electromagnetic radiation to maintain the temperature of said light curable material within said housing at between about 120° F. and about 250° F. and to substantially evenly cure said light curable material while rotating said light curable material.

17. The method of claim 16 wherein said light source is operable using at least 200 watts of power to emit electromagnetic radiation, and provide at least about 50 milliwatts per square centimeter at a distance of about 10 cm.

* * * * *